US009903796B2

(12) United States Patent
Lee et al.

(10) Patent No.: US 9,903,796 B2
(45) Date of Patent: Feb. 27, 2018

(54) METHOD FOR REVERSIBLE FIXATION OR SELECTIVE LYSIS OF CELL USING PHOTOCLEAVABLE POLYMER

(71) Applicant: Samsung Electronics Co., Ltd., Suwon-si, Gyeonggi-do (KR)

(72) Inventors: Hun-joo Lee, Hwaseong-si (KR); Yeon-jeong Kim, Yongin-si (KR); Dong-hyun Park, Chuncheon-si (KR); Jong-myeon Park, Incheon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 4 days.

(21) Appl. No.: 14/323,812

(22) Filed: Jul. 3, 2014

(65) Prior Publication Data

US 2015/0148243 A1 May 28, 2015

(30) Foreign Application Priority Data

Nov. 22, 2013 (KR) .................. 10-2013-0143062

(51) Int. Cl.
*G01N 1/30* (2006.01)

(52) U.S. Cl.
CPC ......... *G01N 1/30* (2013.01); *G01N 2001/305* (2013.01)

(58) Field of Classification Search
None
See application file for complete search history.

(56) References Cited

U.S. PATENT DOCUMENTS

| | | |
|---|---|---|
| 6,261,782 B1 | 7/2001 | Lizardi et al. |
| 6,436,705 B1 * | 8/2002 | Bakaltcheva ........ A01N 1/0221 435/366 |
| 6,677,121 B2 | 1/2004 | Latimer et al. |
| 6,960,447 B2 | 11/2005 | Jakobovits |
| 7,294,367 B2 | 11/2007 | Barron et al. |
| 7,569,392 B2 | 8/2009 | Levy et al. |
| 2002/0106649 A1 | 8/2002 | Lizardi et al. |
| 2002/0119578 A1 | 8/2002 | Zaffaroni et al. |
| 2002/0151085 A1 | 10/2002 | Zaffaroni et al. |
| 2009/0250615 A1 | 10/2009 | Oldham et al. |
| 2011/0129878 A1 | 6/2011 | Rothschild et al. |
| 2011/0306086 A1 | 12/2011 | Nitta |
| 2012/0071338 A1 | 3/2012 | Bowman et al. |
| 2012/0329061 A1 | 12/2012 | Mego et al. |
| 2013/0052653 A1 * | 2/2013 | Stein ................ G01N 33/54346 435/7.1 |

FOREIGN PATENT DOCUMENTS

KR 2009-0065139 A 6/2010

OTHER PUBLICATIONS

Tang et al., Controlling RNA Digestion by RNase H with a Light-Activated DNA Hairpin; Angewandte Chemie Int. Ed., vol. 45, pp. 3523-3526, 2006.*
He et al., Quantitation of circulating tumor cells in blood samples from ovarian and prostate cancer patients using tumor-specific fluorescent ligands, *Int. J. Cancer*, 123: 1968-1973 (2008).
Molecular Probes™ Handbook, Chapter 5, "Crosslinkable and Photoactivatable Reagents" (2010).

* cited by examiner

*Primary Examiner* — Addison D Ault
(74) *Attorney, Agent, or Firm* — Leydig, Voit & Mayer, Ltd.

(57) ABSTRACT

A photocleavable polymer comprising a photocleavable linker and a polymer having a functional group that binds to a protein, lipid, sugar of a cell, or any combination thereof, as well as a method of selectively lysing cells by incubating a sample comprising two or more cells with the photocleavable polymer to reversibly fix the cells; selectively irradiating the fixed cells or a target or non-target cell among the fixed cells to cleave the photocleavable polymer; and adding a cell lysis solution to selectively lyse the irradiated cells.

9 Claims, 8 Drawing Sheets

METHOD FOR REVERSIBLE FIXATION OR SELECTIVE LYSIS OF CELL USING PHOTOCLEAVABLE POLYMER

RELATED APPLICATION

This application claims the benefit of Korean Patent Application No. 10-2013-0143062, filed on Nov. 22, 2013, in the Korean Intellectual Property Office, the disclosure of which is incorporated by reference.

BACKGROUND

1. Field

The present disclosure relates to methods of reversible fixation or selective lysis for selectively lysing target cells or selectively removing non-target cells.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 888 bytes ASCII (Text) file named "716572_ST25.TXT," created Jul. 3, 2014.

2. Description of the Related Art

Cells are basic units of the human body and have different forms for respective organs. Diagnosis of a disease is generally possible through biopsy; however, due to the recent increase in the precision of cytoscopy, a simple and precise diagnosis became possible. Separating target cells or removing undesired cells from a sample in which cells have various properties, such as a blood sample, is necessary for cell counting, identifying shapes and properties of cells, enzyme immunoassay for identifying proteins on cell surfaces or in cell interiors, single cell analysis, or genetic analysis.

Circulating tumor cells (CTC) are a small quantity of tumor cells in blood of a metastatic cancer patient. Detection of tumor cells in blood or analysis of tumor cells separated from blood is important for predicting early diagnosis of cancer, early diagnosis of metastasis, or possibility of recurrence. However, the tumor cells in blood exist in a very small quantity and the cells are fragile, presenting difficulties in detection and identification of CTCs.

During the separation of target cells, when a recovery rate of the target cells is increased, a great number of cells that are not desired may also be separated, which decreases the purity of target cells. When the purity is increased, the recovery rate of the target cells may be decreased. In a molecular analysis of the target cell, increased purity of the target cells increases precision of the molecular analysis and a high recovery rate of the target cells determines the limit of detection (LOD) and increases separability of target cells from undesired cells (e.g., normal blood cells). Also, the numbers of separated target cells and unwanted cells, act as a standard for precise diagnosis of subsequent molecular analyses. For example, when there is no separated target cancer cell, the results of the subsequent molecular analyses may comprise analytic results of undesired, normal cells instead of the target cells. Even when there are separated target cells, when there are too many normal cells separated along with the target cells difficulties in a precise molecular analysis of the target cells may arise due to interference from the normal cells.

Accordingly, a method of precisely analyzing the number of cancer cells while performing a molecular analysis, simultaneously, is needed.

SUMMARY

Provided herein is a photocleavable polymer comprising a photocleavable linker and a polymer having a functional group that binds to a protein, lipid, sugar of a cell, or any combination thereof.

Also provided is a method of reversibly fixing cells, the method comprising incubating a sample comprising cells with a photocleavable polymer to reversibly fix the cells, wherein the photocleavable polymer comprises a photocleavable linker and a polymer having a functional group capable of binding to protein, lipid, or sugar of the cells, or any combination thereof.

Also provided is a method of selectively lysing cells by incubating a sample comprising two or more cells with the photocleavable polymer to reversibly fix the cells; selectively irradiating the fixed cells or a target or non-target cell among the fixed cells to cleave the photocleavable polymer; and adding a cell lysis solution to selectively lyse the irradiated cells.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
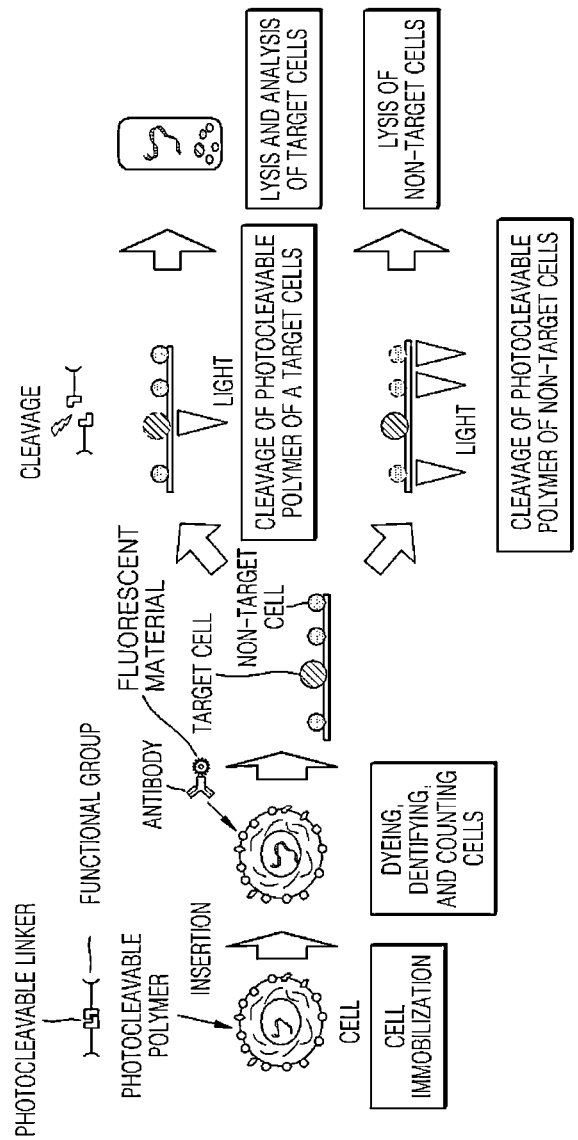
FIG. 1 is a schematic of a method of reversible immobilization or selective lysis of cells by using a photocleavable polymer.
Figure 2A:
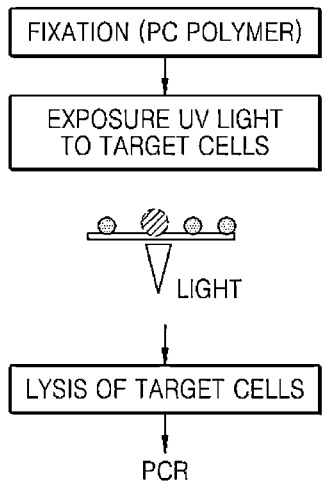
FIGS. 2A to 2D are flow charts showing embodiments of a reversible fixation, selective lysis, and selective analysis of cells by using a photocleavable polymer of the cells.
Figure 2B:
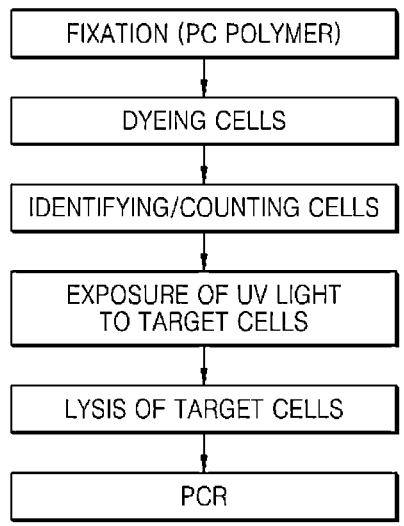
Figure 2C:
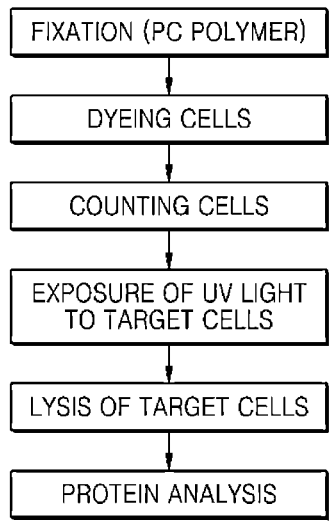
Figure 2D:
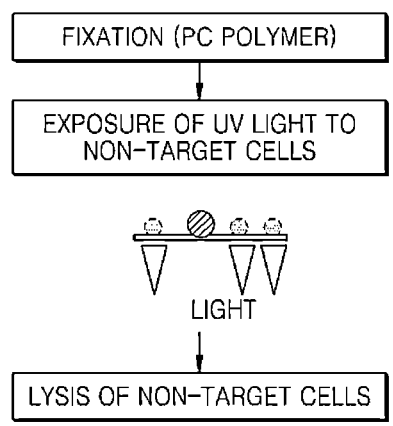
Figure 3:
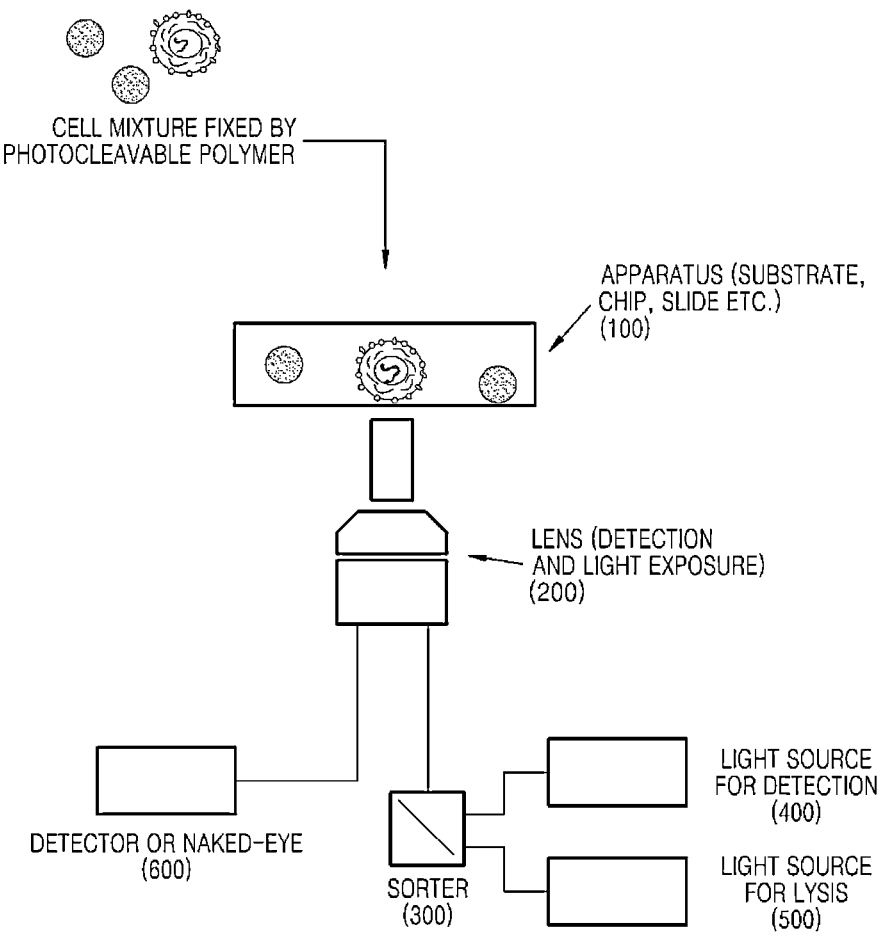
FIG. 3 shows an embodiment of a device for selectively lysing cells.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

Provided is a composition comprising a photocleavable polymer, wherein the photocleavable polymer comprises a photocleavable linker and a polymer having a functional group that binds to a protein, lipid, sugar of a cell, or any combination thereof.

The term "reversible" refers to the capability of returning an object to its original state.

The term "fixation" refers to manipulation of a biological sample or a specimen to maintain the present state of the biological sample or specimen without change. The fixation may be, for example, a physical fixation such as thermal fixation or freeze-drying, or a chemical fixation by using a reagent.

The photocleavable polymer (PC polymer) refers to a polymer that is cleavable by light. The light may be, for example, UV rays or x-rays.

The photocleavable polymer includes a photocleavable linker. The photocleavable linker may be, for example, a compound including a maleimide group, a 2-nitobenzyl group, a (coumarin-4-yl)methyl group, or any combination thereof. The photocleavable linker may be, for example, a compound that may be cleavable by UV rays or x-rays.

The photocleavable polymer may include a polymer having a functional group capable of binding to protein, lipid, sugar, or any combination thereof of a cell. The functional group may bind to a protein, lipid, sugar, or any combination thereof of a cell. For example, the functional group may be an amine group, a thiol group, an N-hydroxysuccinimide (NHS) group, an aldehyde group, an isocyanate group, an epoxide group, an isothiocyanate group, a carboxyl group, a nitrophenyl carbonate (NPC) group, an acrylate group, a hydrazide group, a halide group, a maleimide group, an ortho-pyridilsulfide (OPSS), a vinylsulfone group, a silane group, or any combination thereof. As used herein "polymer" refers to a compound including a plurality of repeat units in the structure thereof. The polymer may be, for example, polyethylene glycol (PEG), poly(L-lysine), polyacrylamide, or any combination thereof.

According to an embodiment, the composition may be used to reversibly fix the cells. The functional group of the photocleavable polymer and the protein, lipid, sugar, or any combination thereof of a cell may be bound to fix the cells. When the linker of the photocleavable polymer is cleaved, the photocleavable polymer may be cleaved as well. Depending on the cleavage of the photocleavable polymer, the cells may be reversibly fixed. When the photocleavable polymer is used, the cells may be selectively fixed. For example, a composition including the photocleavable polymer may be used to fix the cells and light (e.g., radiation) may be applied to the cells to selectively fix the cells.

According to an embodiment, the composition may be used to selectively lyse the cells. The cells fixed by the photocleavable polymer may not be lysed by a cell lysis solution prior to cleaving the photocleavable polymer. After the photocleavable polymer is cleaved, the cells fixed by the photocleavable polymer may be lysed by the cell lysis solution. When the photocleavable polymer is used, the cells may be selectively lysed. For example, the composition including the photocleavable polymer may be used to immobilize two or more cells and light (e.g. radiation) may be selectively applied to the two or more cells or some portion thereof that have been fixed, and the cell lysis solution may be added to the reactants obtained therefrom to only lyse cells that light has been selectively applied to. When target cells are selected, the target cells may be selectively lysed and a cell lysate may be may be obtained therefrom to analyze nucleic acid, protein, lipid, and sugar from the target cells. When undesired non-target cells are selected, the non-target cells may be lysed to remove the same and obtain intact target cells.

Provided is a method of reversibly fixing cells, the method including incubating a sample including the cells with the photocleavable polymer to reversibly fix the cells, wherein the photocleavable polymer includes a photocleavable linker and a polymer having a functional group capable of binding to protein, lipid, sugar, or any combination thereof of the cells.

The photocleavable polymer, the photocleavable linker, the functional group, the polymer, reversibility, and fixation are the same as described above.

The cell may be a nerve cell, an epithelial cell, a germ cell, an immune cell, a muscle cell, a cancer cell, or any combination thereof. The cancer cell may be a blood circulating tumor cell, a cancer stem cell, or a general cancer cell. The cell may be a cancer cell or a tumor cell selected from the group consisting of bladder cancer, breast cancer, cervical cancer, cholangiocarcinoma, colorectal cancer, endometrial cancer, esophageal cancer, gastric cancer, head and neck cancer, kidney cancer, liver cancer, lung cancer, nasopharyngeal cancer, ovarian cancer, pancreatic cancer, gallbladder cancer, prostate cancer, thyroid cancer, osteosarcoma, rhabdomyosarcoma, synovial sarcoma, Kaposi's sarcoma, leiomyosarcoma, malignant fibrous histiocytoma, fibrosarcoma, adult T-cell leukemia, lymphoma, multiple myeloma, neuroblastoma glial astrocytoma, melanoma, mesothelioma, and Wilm's tumor.

The sample may be body fluid. The body fluid may be, for example, urine, mucus, saliva, tears, plasma, serum, sputum, spinal fluid, pleural fluid, nipple aspirates, lymph, respiratory fluid, serous, genitourinary fluid, breast milk, lymphatic fluid, semen, cerebrospinal fluid, body fluid in the organ system, ascites, cystic tumor fluid, amniotic fluid, or any combination thereof. A subject may be a mammal such as a human.

The incubation may be performed at a temperature of 4° C. or at room temperature. During the incubation, inversion, vortexing, agitation, or any combination thereof may be performed.

The method may further include selectively irradiating reversibly fixed cells with light to cleave the photocleavable polymer. When light is selectively applied to the cells, the cells that have been exposed to the light are no longer fixed by the PC polymer, but the cells that have not been exposed to the light maintain a fixed state.

The light may be, for example, UV rays or X-rays. The wavelength of the light may be about 10 nm to about 400 nm, about 100 nm to about 400 nm, about 200 nm to about 400 nm, or about 300 nm to about 400 nm.

The method may further include counting, dyeing, or detecting the reversibly fixed cells. The cells that are fixed may be counted, dyed, or detected to measure the number of all cells or the target cells in the sample, or the target cells may be selected. The counting, dyeing, or detection may be performed according to the method known in the art. The dyeing or the detection may be performed by using an antibody conjugated to a fluorescent material.

Provided is a method of selectively lysing cells, the method including:

incubating a sample including two or more cells and a photocleavable polymer to reversibly fix the cells, wherein the photocleavable polymer includes a photocleavable linker and a polymer having a functional group that binds to protein, lipid, sugar, or any combination thereof of the cells;

selectively irradiating light to the fixed cells, to a target cell among the fixed cells, or to a non-target cell among the fixed cells to cleave the photocleavable polymer to obtain a reactant;

adding a cell lysis solution to the reactant to selectively lyse the irradiated cells.

The cells, sample, incubation, photocleavable polymer, photocleavable linker, functional group, polymer, reversibility, and fixation are the same as described above.

The method selectively irradiating light to the fixed cells, to a target cell among the fixed cells, or to a non-target cell among the fixed cells to cleave the photocleavable polymer to obtain a reactant. When light is selectively irradiated to the two or more cells that are fixed, the cells exposed to the light may not be fixed, but the cells exposed to the light may maintain a fixed state. The target cells that are exposed to light may additionally be lysed by the cell lysis solution. The method may include selectively lysing the target cells among the two or more cells that are fixed. The method may further include analyzing nucleic acid, protein, lipid, sugar, or any combination thereof of the target cells that are lysed. The analysis may be performed according to the method known in the art. For example, analyzing the nucleic acid may be performed by using a polymerase chain reaction (PCR), nucleic acid sequence-based amplification (NASBA), ligase chain reaction (LCR), strand displacement amplification (SDA), multiple displacement amplification (MDA), rolling circle amplification (RCA), or any combination thereof. For example, analyzing the protein may be performed by using electrophoresis, immunoblotting, enzyme-linked immunosorbent assay (ELISA), protein chip analysis, mass spectrometry, immunoprecipitation, or any combination thereof. When the non-target cell is selectively lysed, the non-target cell may be selectively removed from the reactants. The method may further include obtaining an intact target cell from the reactants.

The method may further include counting, dyeing, or detecting the two or more fixed cells. The counting, dyeing, or detecting is the same as described above.

The method includes adding a cell lysis solution to the reactant to selectively lyse the irradiated cells. The method may involve irradiating target cells. When light is applied to the target cells, the target cells may return to the original state, but non-target cells may maintain the fixed state.

When the composition for reversibly fixing the cells and the method of reversibly fixing and selectively lysing the cells by using the photocleavable polymer are used, desired target cells may be selectively lysed to use the cell lysate obtained therefrom in a subsequent analysis and undesired non-target cells may be selectively lysed to remove the non-target cells. Also, the counting, identification, detection, and target cell analysis may be simultaneously performed for the same sample and thus, much information may be obtained from a small amount of the sample. Also, errors caused by the undesired non-target cells may be detected for a precise analysis. Furthermore, a threshold for calculating a Ct (cycle threshold) value may be adjusted according to the number of target cells for a precise analysis.

EXAMPLE 1

Fixation of Cells by Using a Photocleavable Polymer 1-1. Preparing a Photocleavable Polymer A heterobifunctional photocleavable linker of Formula 1 below was prepared.

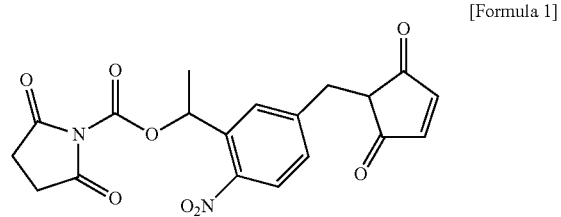 [SMILES: CC(OC(=O)N1C(=O)CCC1=O)c1cc(CC2C(=O)C=CC2=O)ccc1[N+](=O)[O-]]

[Formula 1]

5 µmol of the heterobifunctional photocleavable linker was dissolved in 100 µl of dimethylformamide (DMF) to prepare 5 µmol of heterobifunctional photocleavable linker in 100 µl of DMF.

8-arm-PEG-thiol (Creative PEGWorks) of Formula 2 below having a molecular weight of 40 kDa was dissolved in 1 ml of 1×PBS (phosphate buffered saline) buffer to prepare 625 nmol of 8-arm-PEG-thiol in 1 ml of 1×PBS buffer.

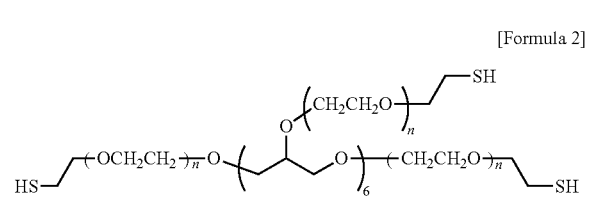

[Formula 2]

The heterobifunctional photocleavable linker prepared above and 8-arm-PEG-thiol were incubated for 2 hours at a temperature of 4° C. to bind a maleimide group of the heterobifunctional photocleavable linker and a thiol group of 8-arm-PEG-thiol. A polymer in which the heterobifunctional photocleavable linker and 8-arm-PEG-thiol are bound was used as a photocleavable (PC) polymer.

1-2. Fixation of Cells by Using a Photocleavable Polymer and Confirmation of the Same Lung cancer cell line HCC827 cells were suspended in 1× PBS buffer and an injection needle was used to separate the same into single cells. 100 µl of the PC polymer prepared as described in Example 1-1 or 1% (w/v) paraformaldehyde (PFA) (Sigma-Aldrich) as a positive control group was added to 2 ml of cell solution and then incubated at room temperature for 2 hours to fix the cells. The cells that were fixed were washed with 1×PBS buffer.

To identify the extent of the fixation of the cells, a cell lysis solution was added to the cells that were fixed and then incubated for 3 minutes at room temperature. As the cell lysis solution, a surfactant solution of 0.1% (w/v) TRITON X-100® (Thermo Scientific) or an alkaline solution of 0.2 N NaOH (Sigma-Aldrich) was used. After the incubation, the number of intact cells was measured by using a microscope.

Figure 4:
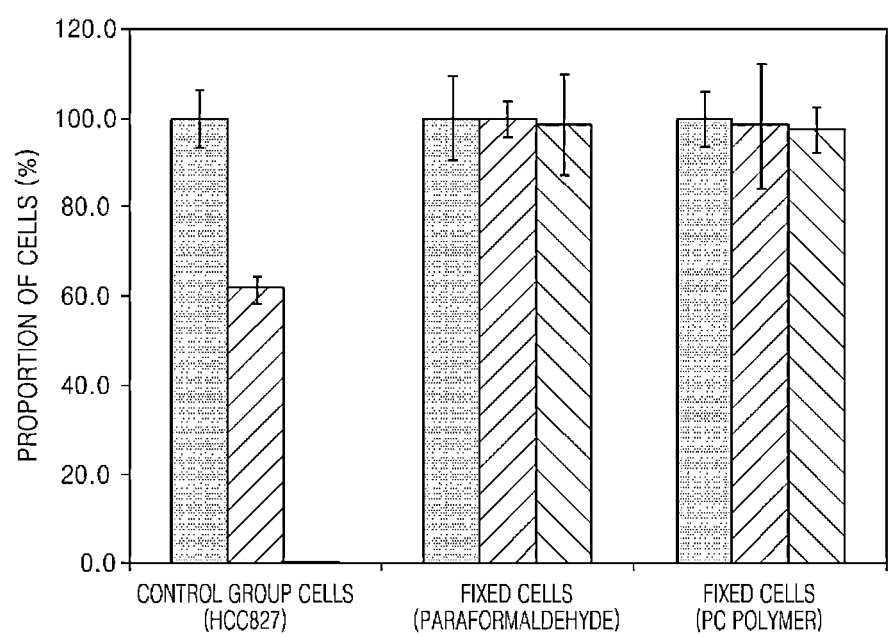
FIG. 4 is a graph showing a proportion (%) of intact cells calculated after lysing cells fixed (☐: initial, ☒ : 0.1% (w/v) TRITON X-100, and ☒ : 0.2 N NaOH)

The number of initial cells before treatment with the cell lysis solution was set at 100% to calculate the proportion of the intact cells and results thereof are shown in FIG. 4 and Table 1 (□: initial, 0.1% (w/v) TRITON X-100, and 0.2 N NaOH).

TABLE 1

| | | Proportion of cells intact (%) |
|---|---|---|
| Control group cells (HCC827) | Initial | 100.0% |
| | 0.1% (w/v) TRITON X-100 | 62.1% |
| | 0.2N NaOH | 0.0% |
| Fixed cells (paraformaldehyde) | Initial | 100.0% |
| | 0.1% (w/v) TRITON X-100 | 100.0% |
| | 0.2N NaOH | 98.6% |
| Fixed cells (PC polymer) | Initial | 100.0% |
| | 0.1% (w/v) TRITON X-100 | 98.3% |
| | 0.2N NaOH | 97.5% |

As shown in FIG. 4 and Table 1, when the control cells that were not fixed were treated with a surfactant, some cells were lysed, and when the cells that were not fixed were treated with an alkaline solution, almost all of the cells were lysed. However, cells that were fixed using a PC polymer remained intact when treated with the surfactant or the alkaline solution. The results observed for PC fixing were similar to the results observed when the cells were fixed with paraformaldehyde. Accordingly, it was confirmed that the cells were thoroughly fixed by the PC polymer.

EXAMPLE 2

Cleavage of a Photocleavable Polymer in Cells Fixed by the Photocleavable Polymer Cells fixed by a PC polymer were exposed to UV light to determine whether the photocleavable polymer was cleavable.

As described in Example 1-2, HCC827 cells were fixed by using the PC polymer. The cells that were fixed were exposed to UV light having a wavelength of 365 nm at 100 J/cm$^2$. An alkaline solution of 0.2 N NaOH (Sigma-Aldrich) was added to the cells exposed to UV light and then incubated for 3 minutes at room temperature. As a negative control group, an alkaline solution of 0.2 N NaOH was added to the HCC827 cells and then incubated for 3 minutes at room temperature. After the incubation, the number of the cells was counted and the results are shown in FIG. 5 and Table 2.

TABLE 2

| | Number of cells |
|---|---|
| Initial | 134.3 |
| Alkaline solution | 132.7 |
| UV exposure + alkaline solution | 1.3 |

Figure 5:
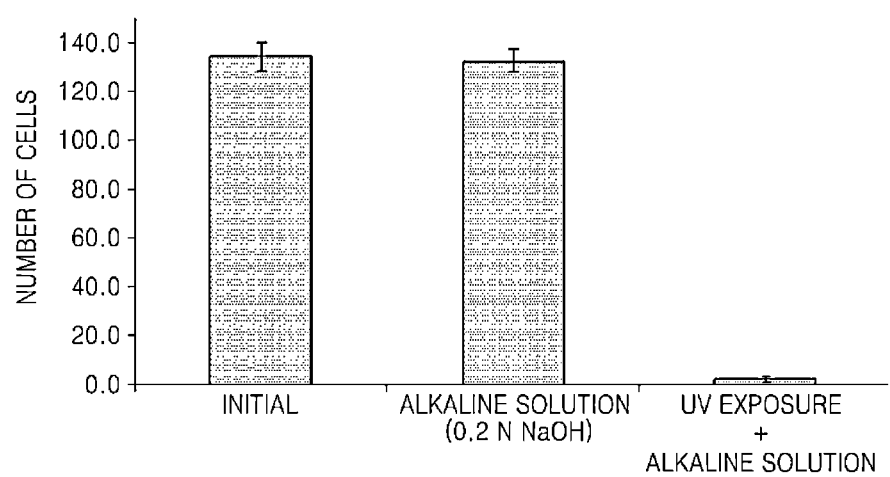
FIG. 5 is a graph showing the number of cells that are fixed by using a PC polymer, exposed to ultraviolet (UV) light and then treated with a cell lysis solution.

As shown in FIG. 5 and Table 2, when the cells that were fixed were treated with the alkaline solution, the cells remained intact; however, when the cells were exposed to UV light and then treated with the alkaline solution, the cells were completely lysed. Accordingly, it was confirmed that after the cells fixed with PC polymer are exposed to UV light, the cells may be lysed by using an alkaline solution.

EXAMPLE 3

Selective Lysis of Cells by Using a Photocleavable Polymer

Cells fixed by PC polymer were exposed to UV light to determine whether the cells may be selectively lysed.

HCC827 cells were disposed on a slide glass. As described in Example 1-2, the HCC827 cells were fixed by using the PC polymer. UV light having a wavelength of 365 nm was irradiated at 100 J/cm$^2$ to one portion of the slide glass. An alkaline solution of 0.2 N NaOH (Sigma-Aldrich) was applied to the slide glass and then incubated for 3 minutes at room temperature. After the incubation, the cells were identified by using an optical microscope (Olympus) and an image thereof is shown in FIG. 6.

Figure 6:
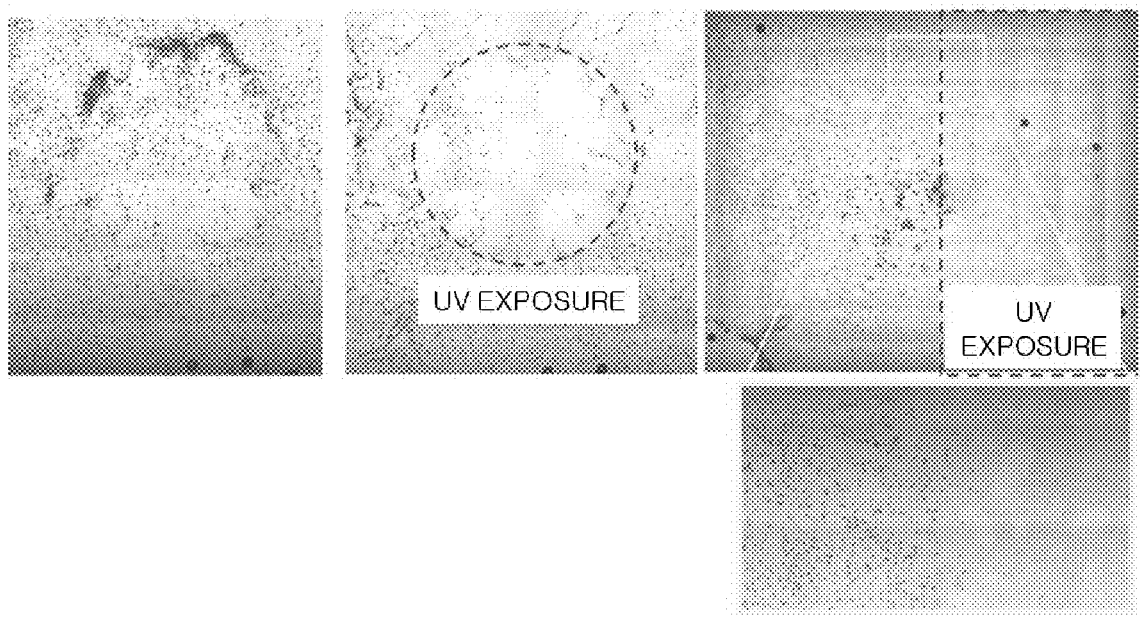
FIG. 6 is an image showing selective lysis of cells fixed by a PC polymer, which are exposed to UV light and then treated with a cell lysis solution.

As shown in FIG. 6, the cells that were fixed were lysed in a portion exposed to UV light, and the cells in a portion that was not exposed UV light were not lysed and remained intact. Accordingly, it was confirmed that the cells fixed by the PC polymer were selectively exposed to UV light such that the cells may be selectively lysed.

EXAMPLE 4

Lysis Efficiency of Cells Fixed by Using a Photocleavable Polymer and then Exposed to UV Light When cells fixed by a PC polymer were exposed to UV light to lyse the cells, cell lysis efficiency was determined by PCR amplification of nucleic acid derived from the cells that were lysed.

In the first group, an alkaline solution of 0.2 N NaOH was added to 2×10$^5$ of HCC827 cells and then incubated for 3 minutes. The reactants were centrifuged for 3 minutes at a speed of 800×g and a supernatant was obtained therefrom.

In the second group, 1% (w/v) paraformaldehyde was added to 2×10$^5$ of HCC827 cells and then incubated at a temperature of 4° C. for 30 minutes to fix the cells. An alkaline solution of 0.2 N NaOH was added to the cells that were fixed and then incubated for 3 minutes. The reactants obtained therefrom were centrifuged for 3 minutes at a speed of 800×g and a supernatant was obtained therefrom.

In the third group, 10 mM PC polymer was added to 2×10$^5$ of HCC827 cells and then incubated at a temperature of 4° C. for 30 minutes to fix the cells. An alkaline solution of 0.2 N NaOH was added to the cells that were fixed and then incubated for 3 minutes. The reactants obtained therefrom were centrifuged for 3 minutes at a speed of 800×g and a supernatant was obtained therefrom.

In the fourth group, 10 mM PC polymer was added to 2×10$^5$ of HCC827 cells, incubated at a temperature of 4° C. for 30 minutes to fix the cells. The cells that were fixed were exposed to UV light having a wavelength of 365 nm at 100 J/cm$^2$. An alkaline solution of 0.2 N NaOH was added to the reactants obtained therefrom and then incubated for 3 minutes. The reactants were centrifuged for 3 minutes at room temperature at a speed of 800×g and a supernatant was obtained therefrom.

The supernatants obtained from the first to the fourth groups were mixed with a forward primer (Life Technologies), a reverse primer (Life Technologies), a probe (Life Technologies), and a TAQMAN® Universal Master Mix II (Life Technologies) to prepare a mixture composition. A target sequence was 3p gene, and sequences of the forward primer, the reverse primer, and the probe used were as follows.

```
Forward primer:
                                        (SEQ ID NO: 1)
5'-TCATCAAAGACAAAGCTAGAGATACTAATAAAAGATCTA-3'

Reverse primer:
                                        (SEQ ID NO: 2)
5'-GAAAATTAGTAATCCCCAAATATCATTTAATATACAGTCCATA-3'
```

-continued

Probe (Life Technologies):

(SEQ ID NO: 3)

5'-ACAGCCATAGATGTTTTGG-3'

After incubating the mixture composition at a temperature of 95° C. for 10 minutes, the mixture composition was subjected to a quantitative PCR by repeating 40 cycles, wherein one cycle includes incubation at 95° C. for 15 seconds and at 60° C. for one minute.

Figure 7:
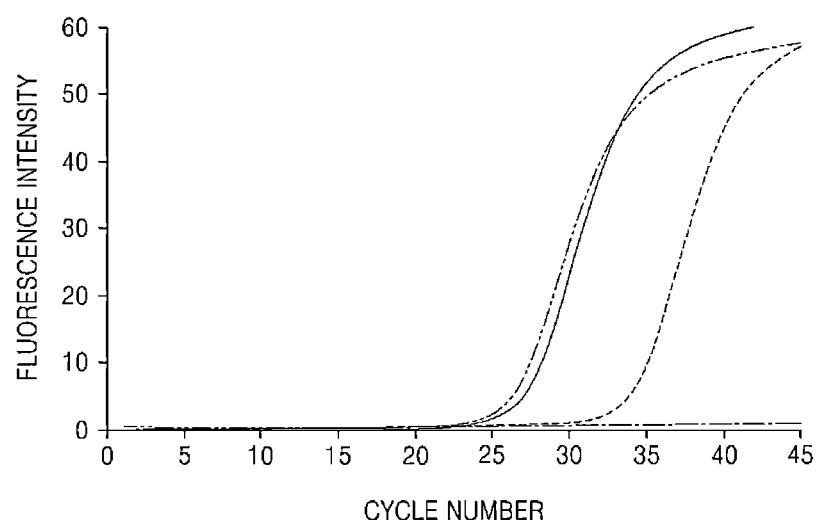
FIG. 7 is a PCR amplification curve obtained from lysing cells fixed by a PC polymer and amplifying nucleic acids derived from lysed cells.

A PCR amplification curve showing fluorescence intensity at about 465 nm to about 510 nm with respect to each cycle number was obtained and results obtained therefrom are shown in FIG. 7 (———: first group, — – —: second group, - - - -: third group, — - - —: fourth group). A Ct (Cycle threshold) value was obtained from the PCR amplification curve and the values are shown in Table 3.

TABLE 3

| Group | Ct value |
|---|---|
| First group (not fixed) | 27.075 |
| Second group (paraformaldehyde fixation) | Not detected |
| Third group (PC polymer fixation) | 31.02 |
| Fourth group (PC polymer fixation and UV exposure) | 26.03 |

As shown in FIG. 7 and Table 3, the Ct value was 27.075 when the cells that were not fixed were lysed and PCR was performed, and 31.02 when the cells fixed by the PC polymer were lysed and PCR was performed. No nucleic acid amplification was detected when the cells were fixed by paraformaldehyde, indicating no lysis. The Ct value was 26.03 when the cells fixed by the PC polymer were exposed to UV light and lysed followed by PCR. Accordingly, when the cells were fixed by the PC polymer and then exposed to UV light, the cells were thoroughly lysed and PCR amplified, and when the cells were not exposed to UV light, the cells were almost not lysed.

As described above, according to the one or more of the above embodiments of the present invention, when the composition for reversibly fixing the cells and the method of reversibly fixing and selectively lysing the cells by using the photocleavable polymer are used, desired target cells may be selectively lysed to use the cell lysate obtained therefrom in a subsequent analysis and undesired non-target cells may be selectively lysed to remove the non-target cells. Also, the counting, identification, detection, and target cell analysis may be simultaneously performed for the same sample and thus, much information may be obtained from a small amount of the sample. Also, errors caused by the undesired non-target cells may be detected for a precise analysis. Furthermore, a threshold for calculating a Ct (cycle threshold) value may be adjusted according to the number of target cells for a precise analysis.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of reversibly fixing and selectively lysing cells, the method comprising:
   incubating a sample comprising cells with a photocleavable polymer to reversibly fix the cells, wherein the photocleavable polymer comprises a photocleavable linker comprising a maleimide group; and a polymer having a functional group that binds to protein, lipid, or sugar of the cells, or any combination thereof, wherein the functional group is, a thiol group; and the polymer is polyethylene glycol PEG;
   selectively irradiating a portion of the reversibly fixed cells with light to cleave the photocleavable polymer, wherein the reversibly fixed cells that have been exposed to the light are no longer fixed by the photocleavable polymer, but the reversibly fixed cells that have not been exposed to the light remain fixed by the photocleavable polymer, and
   adding a cell lysis solution to the sample to selectively lyse the reversibly fixed cells that have been exposed to the light and are no longer fixed by the photocleavable polymer.

2. The method according to claim 1, wherein the light is ultraviolet (UV) rays or X-rays.

3. The method according to claim 1, wherein the light has a wavelength of about 10 nm to about 400 nm.

4. The method according to claim 1, further comprising counting, dyeing, or detecting the reversibly fixed cells.

5. The method according to claim 1, further comprising counting, dyeing, or detecting two or more fixed cells.

6. The method according to claim 1, further comprising analyzing a nucleic acid, protein, lipid, or sugar of the lysed target cell, or any combination thereof.

7. The method according to claim 6, wherein the method further comprises analyzing a nucleic acid of the lysed target cell by polymerase chain reaction (PCR), nucleic acid sequence-based amplification (NASBA), ligase chain reaction (LCR), strand displacement amplification (SDA), multiple displacement amplification (MDA), rolling circle amplification (RCA), or any combination thereof.

8. The method according to claim 6, wherein the method further comprises analyzing a protein of the lysed target cell by electrophoresis, immunoblotting, enzyme-linked immunosorbent assay (ELISA), protein chip analysis, mass spectrometry, immunoprecipitation, or any combination thereof.

9. The method according to claim 1, wherein the method further comprises isolating an intact, fixed target cell from the sample.

* * * * *

SEQUENCE LISTING

<160> NUMBER OF SEQ ID NOS: 3

<210> SEQ ID NO 1
<211> LENGTH: 39
<212> TYPE: DNA
<213> ORGANISM: Artificial Sequence
<220> FEATURE:

```
<223> OTHER INFORMATION: Synthetic (forward primer)

<400> SEQUENCE: 1
tcatcaaaga caaagctaga gatactaata aaagatcta                          39

<210> SEQ ID NO 2
<211> LENGTH: 43
<212> TYPE: DNA
<213> ORGANISM: Artificial Sequence
<220> FEATURE:
<223> OTHER INFORMATION: Synthetic (reverse primer)

<400> SEQUENCE: 2
gaaaattagt aatccccaaa tatcatttaa tatacagtcc ata                     43

<210> SEQ ID NO 3
<211> LENGTH: 19
<212> TYPE: DNA
<213> ORGANISM: Artificial Sequence
<220> FEATURE:
<223> OTHER INFORMATION: Synthetic (probe)

<400> SEQUENCE: 3
acagccatag atgttttgg                                                19
```